(12) United States Patent
Gobeli

(10) Patent No.: US 6,246,893 B1
(45) Date of Patent: Jun. 12, 2001

(54) METHOD AND DEVICE FOR GLUCOSE CONCENTRATION MEASUREMENT WITH SPECIAL ATTENTION TO BLOOD GLUCOSE DETERMINATIONS

(75) Inventor: Garth W. Gobeli, Albuquerque, NM (US)

(73) Assignee: TecMed Incorporated, Albuquerque, NM (US)

( * ) Notice: Subject to any disclaimer, the term of this patent is extended or adjusted under 35 U.S.C. 154(b) by 0 days.

(21) Appl. No.: 08/873,999

(22) Filed: Jun. 12, 1997

(Under 37 CFR 1.47)

(51) Int. Cl.[7] ............................................... A61B 5/00
(52) U.S. Cl. ......................... 600/318; 600/319; 600/336
(58) Field of Search ................................... 600/310, 316, 600/318–320, 322, 323, 336; 356/39–41

(56) References Cited

U.S. PATENT DOCUMENTS

| | | | |
|---|---|---|---|
| 3,958,560 | 5/1976 | March | 128/2 |
| 4,014,321 | 3/1977 | March | 128/2 |
| 4,721,677 | 1/1988 | Clark, Jr. | 435/291 |
| 5,006,342 | 4/1991 | Cleary et al. | 424/445 |
| 5,009,230 | 4/1991 | Hutchinson | 128/633 |
| 5,070,874 | 12/1991 | Barnes et al. | 128/633 |
| 5,139,023 | 8/1992 | Stanley et al. | 128/637 |
| 5,140,985 | 8/1992 | Schroeder et al. | 128/632 |
| 5,209,231 * | 5/1993 | Cote et al. . | |
| 5,313,941 | 5/1994 | Braig et al. | 128/633 |
| 5,321,265 | 6/1994 | Block | 250/343 |
| 5,370,114 | 12/1994 | Wong et al. | 128/633 |
| 5,379,764 | 1/1995 | Barnes et al. | 128/633 |
| 5,383,452 * | 1/1995 | Buchert . | |
| 5,398,681 | 3/1995 | Kuperschmidt | 128/633 |
| 5,433,197 | 7/1995 | Stark | 128/633 |
| 5,435,309 | 7/1995 | Thomas et al. | 128/633 |
| 5,448,992 | 9/1995 | Kuperschmidt | 128/633 |
| 5,568,049 | 10/1996 | Bucholtz | 324/244.1 |
| 5,687,721 * | 11/1997 | Kuhls . | |
| 5,788,632 * | 8/1998 | Pezzaniti et al. | 600/316 |

OTHER PUBLICATIONS

Hecht, E, "Optics, Second Edition," Addison–Wesley Publishing, pp. 316–321, 1987.*

"Microdegree Polarimetry Using A Diode Laser For Glucose Detection", by Marcel J. Goetz Jr., Martin D. Fox and Robert B. Northrop, IEEE 1992, pp. 97–98.

"Noninvasive Glucose Monitoring of the Aqueous Humor of the Eye: Part I. Measurement of Very Small Optical Rotations", by B. Rabinovitch, W. F. March and Robert L. Adams, Diabetes Care, vol. 5, No. 3, May–Jun. 1982, pp. 254–258.

(List continued on next page.)

Primary Examiner—Lee Cohen
Assistant Examiner—David M. Ruddy
(74) Attorney, Agent, or Firm—Cahill, Sutton & Thomas P.L.C.

(57) ABSTRACT

The concentration of glucose in the anterior chamber of an eye is non-invasively measured by guiding a beam through a polarizer (4), a quarter wave plate (6), a polarization modulator (20), and an analyzer (7). After initializing the polarizer and the analyzer to extinguish the beam, it is guided parallel to the iris (56) of the eye (50) and introduced into the anterior chamber (57), wherein it is refracted, impinges on and is reflected from the iris, and exits the anterior chamber approximately collinear with the portion (55A) of the beam incident on the anterior chamber. The beam then is guided onto a detector (10), and a sufficient signal is applied to the polarization modulator to extinguish the beam. The signal represents the glucose concentration in the patient's blood.

41 Claims, 9 Drawing Sheets

OTHER PUBLICATIONS

"A High–precision Photoelectric Polarimeter", by E. J. Gillham, Journal of Scientific Instruments, vol. 34, Nov. 1957, pp. 435–439.

"Noninvasive Glucose Monitoring of the Aqueous Humor of the Eye: Part 1. Measurement of Very Small Optical Rotations", by B. Rabinovitch, W. F. March, and Robert L. Adams, Diabetes Care, vol. 5, No.3, May–Jun. 1982, pp. 254–258.*

"Multispectral polarimetric glucose detection using a single Pockels cell", by Timothy W. King, Gerard L. Cote, Roger McNichols and Marcel J. Goetz, Jr., Optical Engineering, Aug. 1995, vol. 33, No. 8, pp 2746–2753.*

* cited by examiner

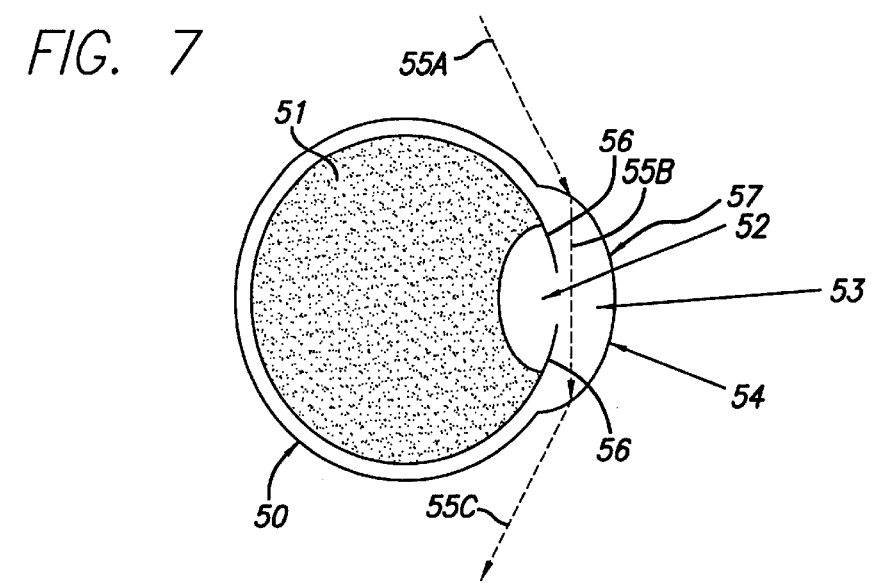
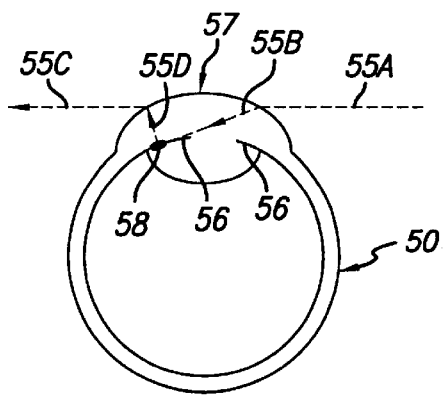
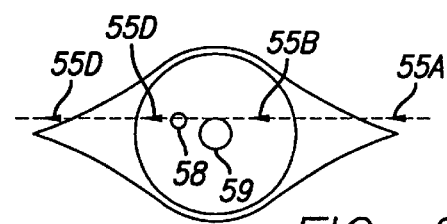
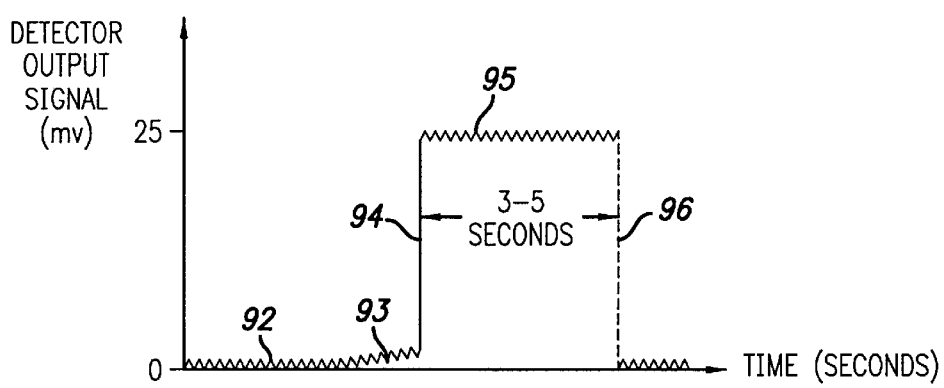

METHOD AND DEVICE FOR GLUCOSE CONCENTRATION MEASUREMENT WITH SPECIAL ATTENTION TO BLOOD GLUCOSE DETERMINATIONS

BACKGROUND OF THE INVENTION

The invention relates to techniques for non-invasive measuring of blood glucose concentration, especially in diabetics.

It is well known that glucose in solution is an optically active material. That is, it will cause the plane of polarization of light traversing the solution to be rotated. The quantitative relationship between the amount of polarization rotation, the glucose concentration, and the optical path length of the solution has been clearly established. It is known that this phenomenon offers the potential for developing a non-invasive blood glucose analyzer.

Diabetes is a disease which entails a large number of associated complications. Retinal deterioration leading to blindness and impaired circulation leading to limb amputation are just two of the more serious complications. Many of these complications result from the large excursions in blood glucose concentrations common to diabetics due to inadequate monitoring of the blood glucose levels. Current methods of diabetic monitoring of blood glucose involve the lancing or sticking of a finger and external measurement of the glucose content of the blood sample. This procedure leaves the diabetic with sore fingers, since the recommended frequency of testing is four or more times per day.

Although many diabetes patients should use the "finger sticking" test to obtain blood for glucose concentration measurements four or more times per day, studies show that very few patients do this unless they absolutely have to, and many patients only do it a few times at the beginning of their treatment until they establish what they think is a pattern in their required medication schedule. They then stop the finger sticking tests and simply take their insulin shots on the assumption that their body chemistry is thereafter constant. This leads to large changes in glucose concentration in the patient's blood, which in turn leads to a variety of serious medical consequences to the patient. For example, it is estimated that in 1996 there were over fifty thousand amputations of limbs due to complications of diabetes in the U.S.

Diabetics recover from cuts and bruises more slowly than do non-diabetics. This very real and basic discomfort causes many diabetics to shirk on the frequency of blood glucose testing, resulting in a higher frequency of complications than otherwise would be the case. A small device that could make blood glucose measurements on a non-invasive basis would be of great value to the diabetic in that it would greatly encourage frequent monitoring of blood glucose levels.

Glucose in solution is an example of an optically active substance. That is, the glucose solution will rotate the plane of polarization of polarized light passing through it in proportion to the path length in the solution and to the concentration of the glucose in the solution. This is expressed mathematically as:

$$\Delta\theta = \alpha * L * C \qquad \text{Eq. 1}$$

Where:

$\Delta\theta$ is the polarization rotation in degrees;

$\alpha$ is the specific rotation constant dependent on the specifics of the glucose type;

$\alpha$=56.5 (35.4) degrees per decimeter (dm) per gram per milliliter for glucose at a wavelength of 633 (780) nanometers L is the path length in the solution in dm, (where 1 dm=10 centimeters (cm);

C is the glucose solution concentration in grams (gm) per milliliter.

For the clinically meaningful glucose concentration range from 50 to 500 mg/dL (milligrams per deciliter) and a path length of 1 cm, the observed rotation ranges from about 0.0028 degrees to about 0.028 degrees for a wavelength of 633 nanometers. As the wavelength is increased the specific rotation $\alpha$ decreases, to a value of 26.3 at a wavelength of 900 nanometers. At that wavelength the rotation in the above case is reduced to 0.0013 and 0.013 degrees respectively. If the assumption is made that about 30% of the path length of radiation passing through living tissue is comprised of blood while the remainder is made up of fat, bone, sinew, etc. then a 1 cm path length through human tissue should produce about 0.001 to 0.01 degrees of polarization rotation. Thus, a useable system must have a basic sensitivity of the order of about 0.0003 degrees, i.e., 1 arc-second, or 5 micro radians.

It is known that human tissue is basically transparent in the wavelength range from about 750 nanometers to about 1800 nanometers. This is the spectral region known as the "overtone" region. It lies between the electronic, or atomic transition, wavelength region on the short wavelength side and the molecular vibrational-absorption region on the long wavelength side. Since there are no fundamental absorption processes in this region, it is found that organic materials basically have quite reasonable optical transmission in this region of the spectrum.

U.S. Pat. No. 5,209,231 by Cote et al. describes a non-invasive glucose sensor which utilizes a pair of polarizers, a quarter wave plate and a motor driven polarizer which produces a constant amplitude phase modulated beam. This beam is split into two beams, one of which passes through the sample and the other which is employed as a reference. By phase demodulation of the two beams, each incident on a different detector, a measure of glucose concentration in an optical cell is determined. Measurements are proposed to be made transversely through the eye's anterior chamber (e.g., 57 in FIG. 3). This approach suffers in sensitivity of measurement (according to the authors) which is probably due to noise problems associated with the motor driven phase modulator as well as other unidentified problems.

"Multispectral Polarimetric Glucose Detection using a Single Pockels Cell", Optical Engineering, Vol. 33, pp 2746 (1994) by King et al. describes a system which employs a pair of polarizers, a quarter wave plate, and a Pockels cell modulator which are configured as a polarization spectrometer. They employed the output from a lock in amplifier which is "filtered using a leaky integrator" and then fed back to a compensator circuit which was eventually summed with the driver oscillator output and then input to the Pockels cell driver to null the AC signal in the system. Again, noise levels in the system represent the major problem in achieving the required sensitivity. The reported data show a scatter that is unacceptable for a working blood glucose sensor.

The angle of incidence of the input beam to the cornea and the exit angle therefrom as shown in FIG. 1 of the King et al. article are so large that the instrumentation, including small turning mirrors or the like, must be positioned very close to the patient's sclera or the soft tissue near the base of his/her nose and the soft tissue at the outer corner of the eye that it is difficult to provide the input beam and to intercept the exit beam, especially with a portable instrument. Furthermore, these angles are sufficiently large that it is difficult to "initialize" the apparatus by rotating the polarizer and analyzer sufficiently to produce the initial extinction of the beam required. The angles required of a prism which would provide the same angle of incidence and exit angle for initial alignment of the apparatus are so large that a suitable prism is very expensive. While the size and shape of the human eye does not vary substantially from person to person, the soft tissue structure surrounding the eye does vary greatly from person to person. This makes it difficult to design support structures for the turning mirrors required to provide the incidence beam and intercept the exit beam.

"Noninvasive Glucose Monitoring of the Aqueous Humor of the Eye: Part I. Measurement of Very Small Optical Rotations", Diabetes Care, Vol. 5, pg 254, by Rabinovitch et al. describes a system having two polarizers, and two Faraday rotator/modulators. In this case there was no quarter wave plate employed in the apparatus. The absence of the waveplate means that their system is vulnerable to ellipticities of polarization which might be produced by mirror or optical surface reflections as well as any problems with scattering by the sample or any surfaces in the optical beam. According to the authors, noise in the system "was sufficiently large to make reading the fourth decimal difficult". Thus a sensitivity of less than one part in 10,000 was achieved. Since it is readily observed that a sensitivity of one part in 100,000 represents the minimally acceptable sensitivity in a practical measurement system, this approach is also unacceptable.

U.S. Pat. Nos. 5,398,681 and 5,448,992 by Kupperschmidt refer to the phase-sensitive measurement of blood glucose and both patents employ (different) systems having a sample and a reference beam which are phase modulated relative to each other. It remains to be demonstrated whether or not successful measurements can be obtained with the Kupperschmidt apparatus.

SUMMARY OF THE INVENTION

Accordingly, it is an object of the invention to provide a device capable of measuring the concentration of an optically active ingredient in a sample.

It is another object of the invention to provide a device capable of measuring an optically sensitive ingredient in biological tissue in a non-invasive manner.

It is another object of the invention to provide an improved apparatus and method for obtaining a null value in making a polarization rotation measurement.

It is another object of the invention to provide an apparatus and method for determining the concentration of an optically active ingredient in the anterior chamber of the eye which avoids inaccuracies due to variation in the optical path length of a beam through the anterior chamber of the eye.

It is another object of the invention to avoid the problems in initializing a measurement apparatus prior to making a glucose concentration measurement based on polarization rotation of a beam in the anterior chamber of an eye.

It is another object of the invention to provide an apparatus and technique to introduce an optical beam into the anterior chamber of the eye and receive the transmitted beam without touching the sclera of the eye or soft tissue around the eye.

It is another object of the invention to provide a device capable of measuring the sucrose concentration of human blood in a non-invasive manner.

It is another object of this invention to provide a new very sensitive and stable polarization spectrometer which has applications in ellipsometry and in certain types of chemical analysis.

Briefly described, and in accordance with one embodiment thereof, the invention provides a system and method for measuring the concentration of an optically active substance, for example glucose, in the anterior chamber of an eye, by guiding a beam, preferably of collimated monochromatic light, through a polarizer oriented in a first direction to polarize the light in a first direction, and then through a polarization modulator and an analyzer oriented in the second direction to polarize the light in a second direction; the beam is guided from the analyzer to a detector, and at least one of the polarizer and the analyzer is adjusted to extinguish light of the beam to prevent it from passing from the analyzer to the detector; after the beam passes through the polarizer, the beam is guided so that it is generally parallel to an iris of the eye as it is introduced into the anterior chamber wherein it is refracted, impinges on the iris, is reflected therefrom, and then exits the anterior chamber approximately collinear with the beam immediately before the point at which it is introduced into the anterior chamber. The beam exiting from the anterior chamber is guided onto the detector. A signal is applied to the polarization modulator just sufficient to extinguish light passing from the analyzer to the detector. The DC signal then represents the concentration of the glucose in the anterior chamber. The beam preferably also is passed through a quarter wave plate after it exits from the polarizer. In one embodiment the orientation of a portion of the beam incident on a cornea of the eye is adjusted until a stable, substantially increased output signal level is produced by the detector. In that embodiment and also in a different embodiment the polarization modulator can be a Faraday rotator, wherein a DC signal and an AC signal are applied to a coil of the Faraday rotator to extinguish light of the beam to prevent it from passing from the analyzer to the detector by shifting the DC signal to a value that produces a null in the AC component of a corresponding output signal produced by the detector. The value of the shifted DC signal then represents the glucose concentration in the anterior chamber. The output signal of the detector is applied to an input of a lock-in amplifier, and the null has been achieved when a DC output of the lock-in amplifier is zero. In the described embodiments the DC signal is a DC current having a value in the range of about 0.01 to 100 milliamperes, and the AC signal is an AC current having a range in the value of about 0.01 to 10 amperes, to thereby greatly reduce noise in the detector output, to the range of a few millivolts or less.

BRIEF DESCRIPTION OF THE DRAWINGS

FIG. 7 is a cross sectional view of a human eye useful in describing the invention.

FIG. 8A is a diagram showing an alternative optical path useful for blood glucose determinations by using the anterior chamber of the eye.

FIG. 8B is a frontal view of the alternative optical path of FIG. 8A.

FIG. 8C is a graph illustrating the detector output signal when the embodiments of the invention according to FIGS. 8A and 8B are utilized.

DETAILED DESCRIPTION OF THE PREFERRED EMBODIMENTS

Figure 1:
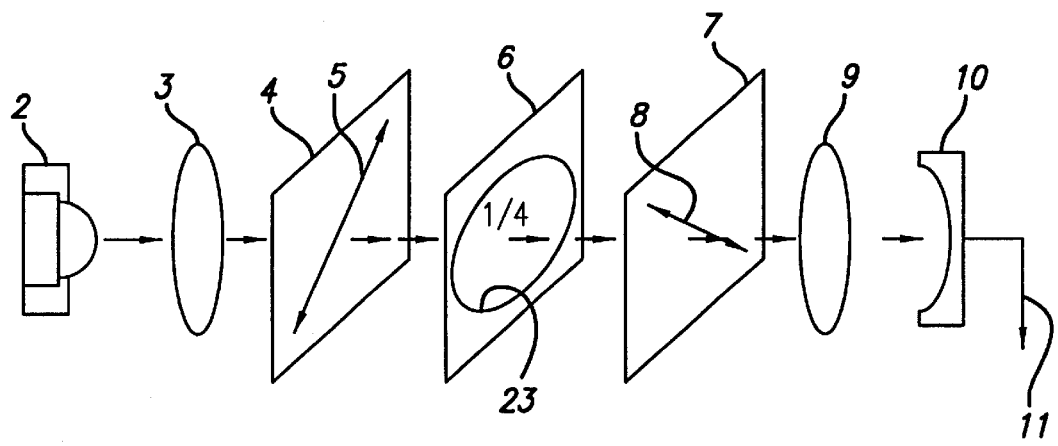
FIG. 1 is a diagram illustrating a conventional polarization spectrometer.

To assemble a small device capable of making rapid and accurate determinations of glucose concentrations under such conditions, it is advantageous to utilize several newly developed components including optical fibers, high Verdet constant glass optical phase modulators, and small, dedicated microprocessors. (A glass with a high Verdet constant is one that has a relatively large amount of polarization rotation under the application of a given magnetic field.)

In one embodiment of the proposed device, light from an LED or laser diode is collimated and polarized. This parallel light beam is passed through a quarter wave plate and subsequently a section of an electro-optic material such as PLZT which acts as a polarization modulator via optically active phase modulation. (Alternatively, a section of high Verdet constant glass can be placed inside a small helical coil of copper wire and, by passing current through the coil, a longitudinal magnetic field is created which acts on the glass to rotate the plane of polarization of the light passing through it. This phenomenon is known as the Faraday effect and the device is known as a Faraday rotator.) The light can be routed to the glucose sample at the selected measurement site by mirrors or by a fiber optic collimator.

The light is collected by a second mirror or optical fiber collimator and is routed through the analyzer, which is rotated so as to obtain total extinction of the light beam. Finally the light is routed to a focusing lens and a silicon detector. The DC voltage applied to the phase modulator or the DC current through the Faraday rotator is adjusted to compensate exactly for the glucose solution rotation, and this DC voltage or current then provides the measure of the phase rotation caused by the glucose in the sample, and hence the glucose concentration therein.

In accordance with the present invention, detector sensitivity is enhanced by the application of a large AC modulation voltage/current superimposed onto the small DC voltage applied to the phase modulator or the DC current applied to the Faraday rotator. Known lock-in amplifier techniques, subsequently described, are employed to optimize the sensitivity or detectivity of the overall system.

One major complicating factor involved in this methodology, for the case that measurement takes place through skin and tissue, lies in the depolarization of the transmitted beam due to scattering of the beam by the non-homogeneous media (bone, sinew, blood platelets, etc.) of the human body. This scattering results in an overall ellipticity of the transmitted beam and a resultant decrease in the precision in the measurement. By introducing a quarter wave plate into the optical system, it is possible to compensate for this depolarization effect and restore the sensitivity of the measuring apparatus. Small errors that may be introduced by misalignment of the components or by small strains in the various elements of the system can be compensated for by means of a pre-measurement calibration procedure and appropriate orientation of the polarizer, analyzer and quarter wave plate.

For the case that the measurement takes place through the anterior chamber of the eye this problem does not exist since the cornea of the eye provides a transparent window into an optically clear sample fluid (the aqueous humor). This is important, because there have been several clinical studies that confirm a direct relationship between a patient's blood-glucose concentrations and glucose concentrations in the aqueous humor of the anterior chamber of the patient's eye.

The proposed optical blood glucose analyzer is based on a modified polarization spectrometer. The components of a basic spectrometer, shown in FIG. 1, include a laser diode or light emitting diode 2 which is a monochromatic light source, the output of which is collimated by a collimating lens 3 and transmitted to a polarizer 4. Arrows 5 indicate the direction of polarization of light passing through polarizer 4. The resulting polarized light passes through a quarter wave plate 6. Feature 23 of quarter wave plate 6 represents the capability of a quarter wave plate to modify the relative phases of polarized light beams to produce elliptically or even circularly polarized light. Quarter wave plate 6 is followed by an analyzer 7, in which arrows 8 represent the direction of polarization of analyzer 7. The light emanating from analyzer 7 passes through focusing lens 9 and is focused onto a suitable detector, such as a silicon photodiode, which produces an output signal 11 that represents the amount of light that is transmitted through the entire spectrometer. For a very carefully oriented polarizer, quarter wave plate, and analyzer system the transmission is about 1 part in 100,000 of the light incident on the first polarizer.

Basic polarization spectrometer 1 is capable of analyzing any combination of linearly and elliptically polarized light. Its precision is limited only by the quality of the polarizers 4 and 7 and the capability of determining the "position" of the intensity minimum at the detector.

Polarizers having extinction ratios of several tens of thousands are now readily available. The extinction ratio is defined as the light intensity transmitted by two parallel oriented polarizers to that transmitted by two perpendicularly oriented polarizers. The precision with which the extinction position of polarizer 4 and analyzer 7 can be measured directly is about 0.3–0.5 degrees due to the gradual change of transmission about the extinction point.

For "crossed" polarizers 4 and 7 (placed at 90 degrees relative to each other), the transmission as a function of $\Delta\theta$ is given by $$I+I_o \sin^2(\Delta\theta), \qquad \text{Eq. 2}$$

which is a slowly varying function about the extinction position ($\Delta\theta=0$). This precision is clearly not satisfactory for the problem at hand.

By alternately rotating analyzer 7 about its null position by plus and minus a few degrees, it is possible to determine positions of equal intensity on each side of the null position and then use the average value of these two readings as the true null position. In this method, the precision is limited by the ability to read divided circles accurately as well as by the precision of the divided circles themselves. The inventor has demonstrated a precision of about plus or minus 0.01 degrees when this method is employed. This precision thus approaches the required value of 0.0003 degrees (or 1 arc second or about 5 micro radians), but remains somewhat short of the desired accuracy.

An additional component referred to as a "modulator/rotator" can be used to measure the rotation of polarization in a totally electronic manner, as opposed to the conventional method of physically rotating polarizer 4 and analyzer 7 to effect the measurement.

Figure 2:
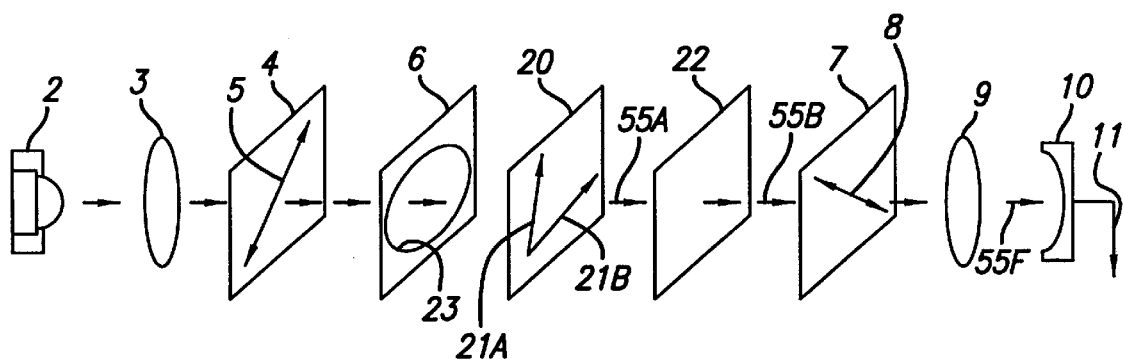
FIG. 2 is a diagram illustrating a blood glucose polarization spectrometer according to the present invention.

FIG. 2 shows the additional components required with those in FIG. 1 for the determination of blood glucose at satisfactory accuracy levels, including a modulator/rotator 20 and a suitable tissue sample 22. There are several devices that can serve as the modulator/rotator. The Faraday effect rotator, described above is one such device. A second device would be a solid state Kerr cell. A Kerr cell is a system in which the electric field is applied transversely to the propagating light beam. The medium of the Kerr cell can range from liquids, such as nitrobenzene, to crystalline materials, such as KDP (potassium di-hydrogen sulfate) or amorphous solids, such as PLZT (lead lanthanum zirconate-titanate). Another candidate device would be a Pockels cell, in which the electric field is applied along the propagation direction in an appropriate crystalline medium, such as again KDP. Arrows 21A and 21B shown in modulator/rotator 20 are simply a diagrammatic symbol to indicate that the plane of polarization is changed by the modulator.

To measure the blood glucose or blood glucose level in tissue sample 22, the apparatus 1A of FIG. 2 is aligned optically, and the quarter wave plate fast axis is manually aligned at 45 degrees to the axis of polarizer 4. (In a quarter wave plate, there are two mutually perpendicular directions or "axes" which lie in the plane of the plate. They are the "fast" and the "slow" axes and correspond to the velocities of the two characteristic polarized waves in the crystal.) Then alternately analyzer 7 and polarizer 4 are successively adjusted until output signal 11 indicates that total extinction is achieved (with no sample present) and with zero activation of modulator/rotator 20.

Then the sample 22 is introduced, and modulator/rotator 20 is activated so as to again produce extinction in the transmitted beam. The amount of DC voltage/current applied to modulator/rotator 20 to achieve this extinction is then a measure of the glucose concentration.

Figure 6:
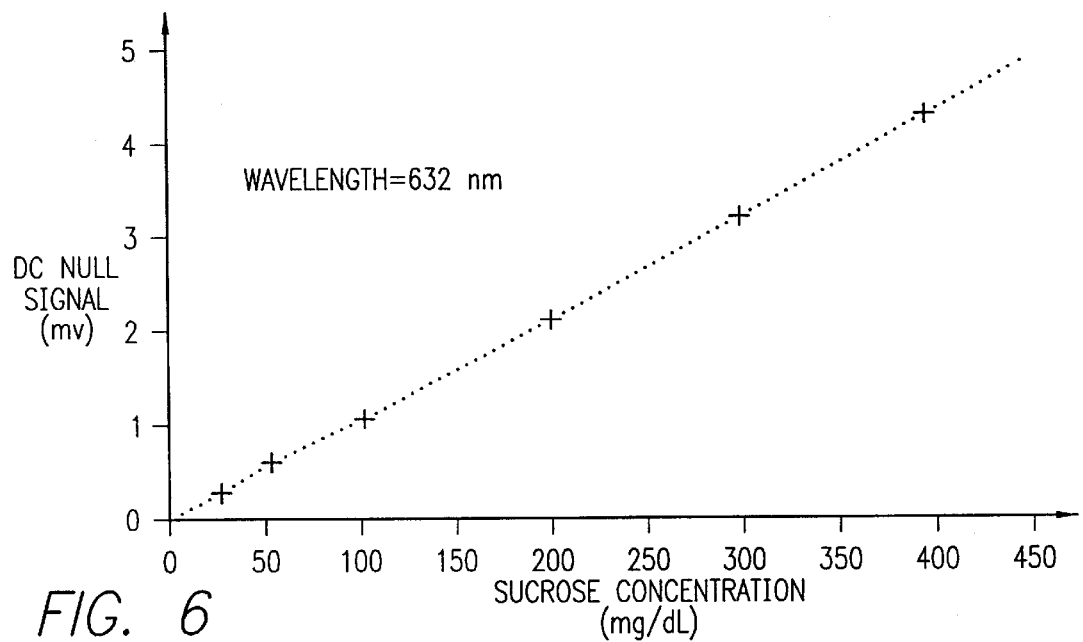
FIG. 6 is a graph indicating the detector output signal versus sucrose concentration.

A series of calibration measurements employing known glucose concentrations in water uniquely establish the relationship between the DC activation voltage/current and the glucose concentrations. The diagram of FIG. 6 shows this relationship.

In the embodiment of FIG. 2 the DC voltage or current activation component applied to the optical phase modulator/rotator 20 has an AC component superimposed on it of sufficient amplitude to cause plus and minus rotation of some few degrees. Then the determination can be made as follows:

The DC component is adjusted so as to produce a precisely equal plus and minus amplitude swing in the AC component. This manual offset movement method has been shown to provide a measurement capability in $\Delta\theta$ of some plus or minus 0.01 degrees when the analyzer position is determined by the reading of a divided circle (this manual approach does not involve any type of modulator/rotator). Such precision, although greatly improved over the pure extinction method, remains inadequate for useful blood glucose determinations. By the use of the electronic phase modulator/rotator and the employment of phase sensitive detection methods a still greater precision of approximately 0.0001 degrees (0.35 arc second or 1.5 micro radians) has been experimentally demonstrated. This sensitivity will provide a precision in blood glucose concentrations of better than 2 mg/dL, which value will permit the determination to be made to better than 5% of even the lowest meaningful concentrations.

Figure 3:
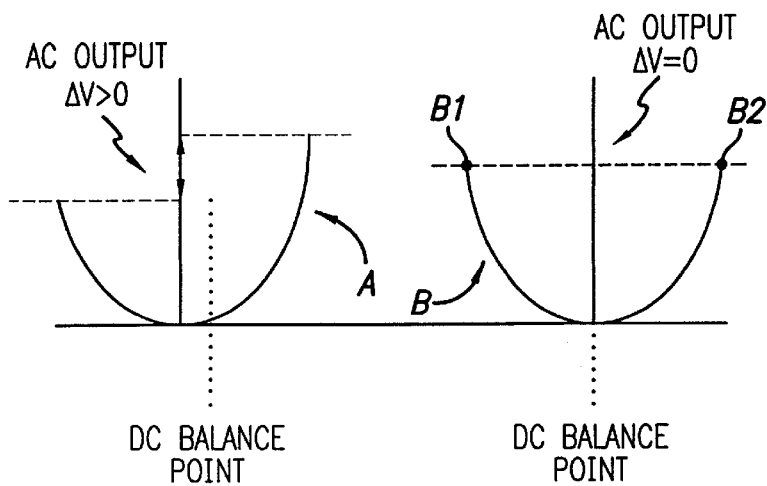
FIG. 3 is a diagram useful in explaining the offset difference method of polarization rotation determination used in the embodiment of FIG. 2.

The method of determining the precise null position is illustrated in FIG. 3, wherein the main curves A and B represent the $\sin^2(\Delta\theta)$ dependence of detector output signal 11 as a function of polarization rotation. Curve A in FIG. 3 shows the output for a DC activation which is offset from true null and the consequent anisotropic output of the detector. Curve B in FIG. 3 shows the situation for an exact null position.

Figure 4:
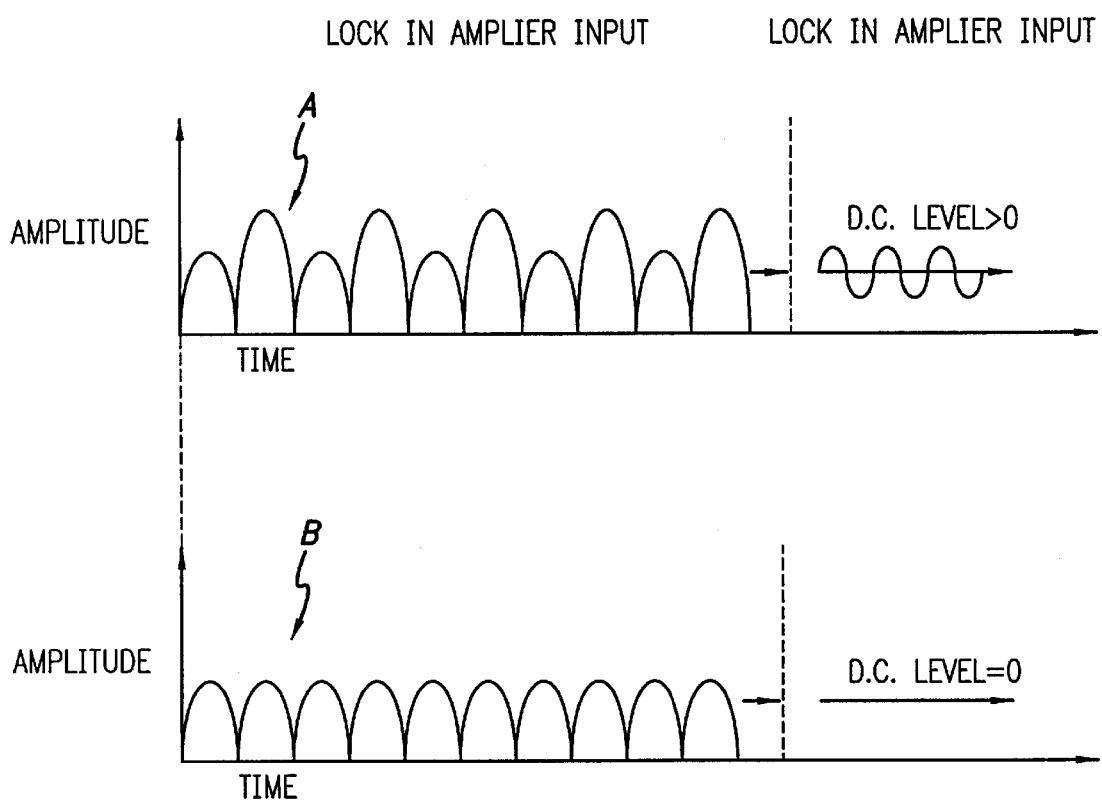
FIG. 4 is a diagram illustrating lock-in amplifier output signal in accordance with the method of FIG. 3.

FIG. 4 shows the output which would derive from a lock-in amplifier being employed in the detector circuit.

I have found that the accuracy of determining the exact DC null position is dependent on how precisely the lock-in zero of the detector output can be located. I also have found that an accuracy of 0.01 millivolts (mv) is observed, while the signal of rotation (for 100 mg/dL glucose concentration) is 1.12 mv; thus a precision of about 1% or about 1 mg/dL has been realized with this methodology.

The method of coupling both an AC and a DC voltage or current component to an optical modulator/rotator so as to avoid the inaccuracies due to various noise sources is described below with reference to FIG. 5. In the measurement configuration, two superimposed signals are applied to the coil of the Faraday rotator 20. An AC sine wave current signal having a frequency of about 475 hertz applied to the coils of the Faraday rotator causes the polarization of the Faraday rotator 20, and hence the detector output signal, to alternately shift to either side of the optical null. A constant DC current also is applied to the coil so as to center the AC fluctuations equally to either side of optical null.

In the experimental embodiments which I have constructed and tested to date, the DC signal is a DC current having a value in the range of about 0.01 to 100 milliamperes, and the AC signal is an AC current having a value in the range of about 0.01 to 10 amperes in order to reduce the noise in the detector output signal on conductor 11 to the range of a few millivolts or less. In miniaturized future devices having redesigned Faraday rotators, the above values will be different. What is probably most important is that the ratio between the AC and DC currents will be from about 10,000 to 1,000,000. This range of ratios of the AC voltage to the DC voltage magnitudes probably will be also applicable if the Faraday rotator is replaced by a Kerr cell or a Pockels cell.

The initial value of the DC current applied to the coil of the Faraday rotator 20 is selected to produce the needed magnetic field through which the laser beam passes. For example, a DC current of approximately 0.1 milliamperes through the coil of the Faraday rotator 20 might produced a desired "bias value" of the magnetic field therein. For the apparatus which I have constructed and tested, an AC modulation voltage of 15 volts peak-to-peak, to thereby produce a 1 ampere peak-to-peak AC modulation current in the Faraday rotator coil having a resistance somewhat less than 15 ohms, was found necessary to achieve the desired sensitivity and accuracy of the DC balance point voltage as shown in curve B of FIG. 3. The $\sin^2$ nature of the polarization modulator or Faraday rotator 20 is that with the foregoing value of AC modulation, the noise present, being superimposed on the detector output signal, has sufficiently negligible effect on the DC balance point shown for curve B in FIG. 3 that the DC balance point current very accurately represents the polarization rotation and hence the glucose concentration in the sample.

This is because for the foregoing 1 ampere value of AC modulation current and 0.02 milliampere value of DC balance point bias current, the slope of curve B in FIG. 3 at points B1 and B2 is sufficiently steep that only a small fraction of the noise superimposed on the AC modulation waveform affects the DC balance point. Stated differently, the projection of the noise component at points B1 and B2 on curve B of FIG. 3 onto the horizontal axis is very small and therefore does not produce an unacceptably large uncertainty or noise voltage on the value of the current applied to the coil of the Faraday rotator to obtain the DC balance point provided that the stability of the AC voltage amplitude is precise to about plus or minus 0.001 volt.

The DC current acts to balance the optical system so that at the positive and negative peaks an equal amount of light is passed. The light passed is converted to a voltage or current by detector 10, and is sent to a lock-in amplifier 45. The lock-in amplifier 45 is phase adjusted such that when Faraday rotator 20 is balanced the output of the lock-in amplifier 45 is zero. Any slight imbalance in the DC null position will yield a non-zero detection output signal.

The DC current corrects for steady-state imbalances in the system and for the DC null point imbalance that is introduced by placing a sample in the optical path. Subtracting the current which is required to null the system at steady state with no sample from the current required to produce null with the sample present gives the current change, or current delta ($\Delta$). It is this delta value which is then interpreted to represent a value of glucose concentration.

Figure 5:
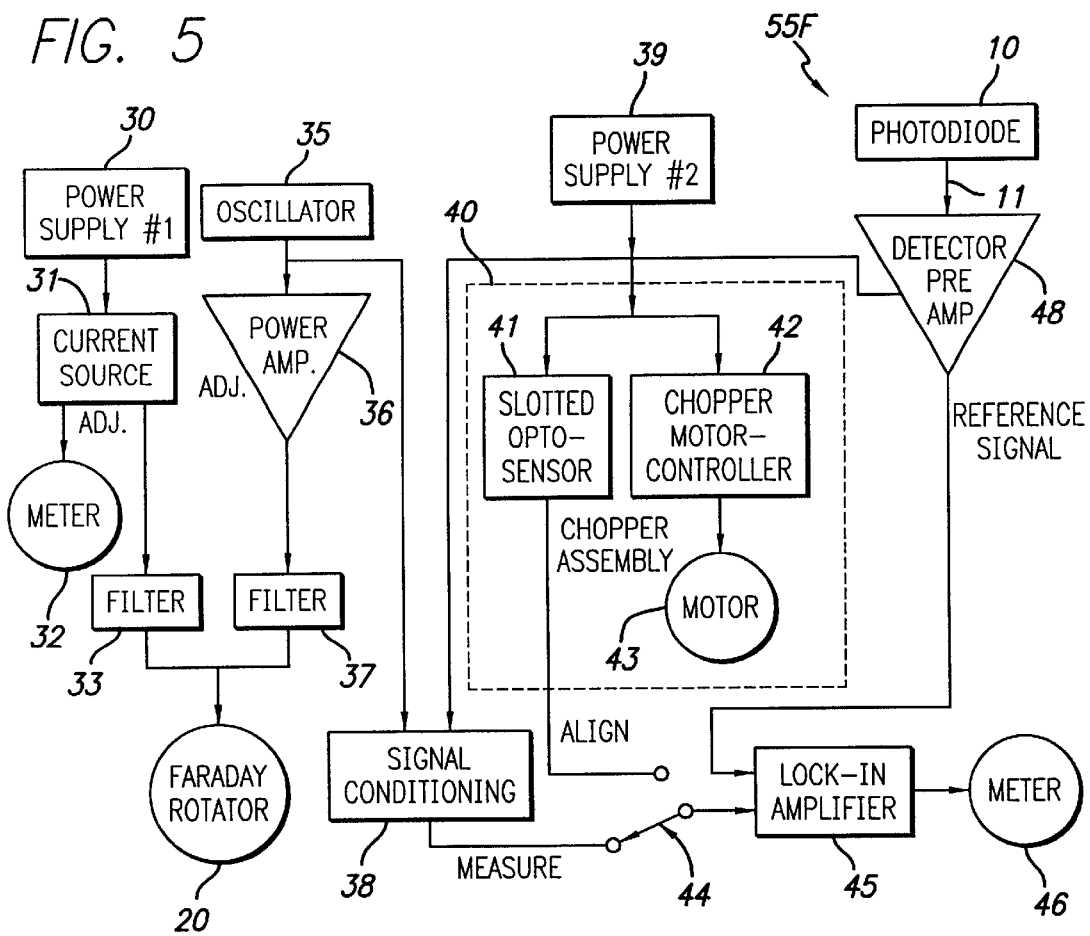
FIG. 5 is a block diagram of the blood glucose analyzer system used in conjunction with the embodiment of FIG. 2.
Figure 5A:
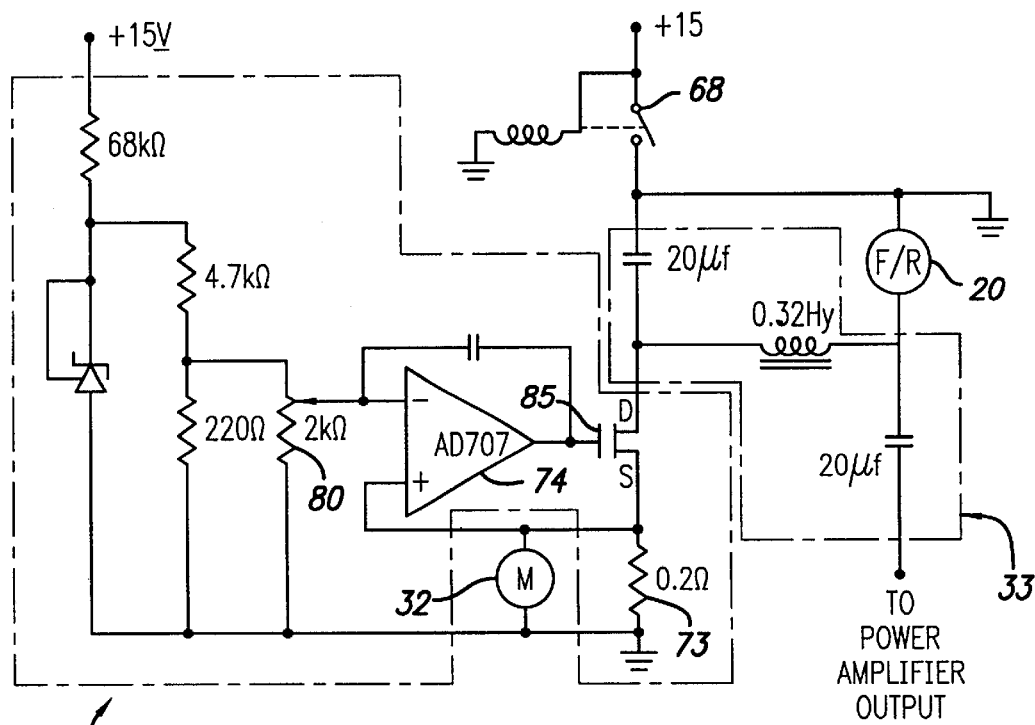
FIG. 5A is a circuit schematic drawing of the current source 31 and filter 33 of FIG. 5.

The DC current source 31 is precisely adjustable from 0 to 500 milliamperes by setting a ten-turn potentiometer 80 (FIG. 5A). This sets a reference voltage that is converted to a current by a voltage-to-current amplifier circuit 30. Feedback is provided through a current sensing resistor 73. This samples the current and converts it back to a voltage which is then compared to the reference.

Precision and stability are attained by using a low DC drift operational amplifier 74, a good voltage reference FET 85, and the ten-turn potentiometer 80. The current sensing resistor is chosen to be a low enough value to avoid self heating effects, which would cause a shift in its resistance. However, the resistor cannot be overly low in value, because the resulting low sensing voltage would cause offsets and drift in the operational amplifier 74 to become a problem. The ground point of the reference FET 85 must connect as directly as possible to the ground point of the current sensing resistor to avoid errors due to resistance in ground lines.

Operational amplifier turn-on transients can cause an unacceptable current spike at the current source output. This is avoided by using a relay 68 which is energized directly from the power supply. The relay contacts engage after about a 10 millisecond delay, allowing the operational amplifier ample time to stabilize. The relay then connects the current source output to the load.

To allow complete independence from other signals, the current source is allowed to float with respect to the system ground. Consequently, this circuit has its own independent power supply 30.

Because the precision of the AC signal waveform is somewhat less critical (even though the waveform amplitude is critical), the AC circuit 35,36 has a voltage output for simplicity. An oscillator 35, set at about 475 Hz, drives a power amplifier 36. (Actually, an oscillator frequency between about 200 and 10,000 Hz would be acceptable.) The amplifier 36 is adjusted to provide about 15 volts peak-to-peak drive signal to Faraday rotator 20.

The filter circuitry 33,37 serves to allow the AC and DC components to combine, and prevents interaction between the AC and DC circuits. In the first filter section 33, DC current is blocked both to and from the output of AC amplifier 36 by a non-polarized low-leakage capacitor in series with the amplifier output. In the second filter section 37, AC feeding back toward the DC current source is highly attenuated by a two pole L-C (inductor-capacitor) network However, DC is allowed to pass from the current source to the load without attenuation. The capacitor in this section is also a low-leakage type and is non-polarized.

Figure 5B:
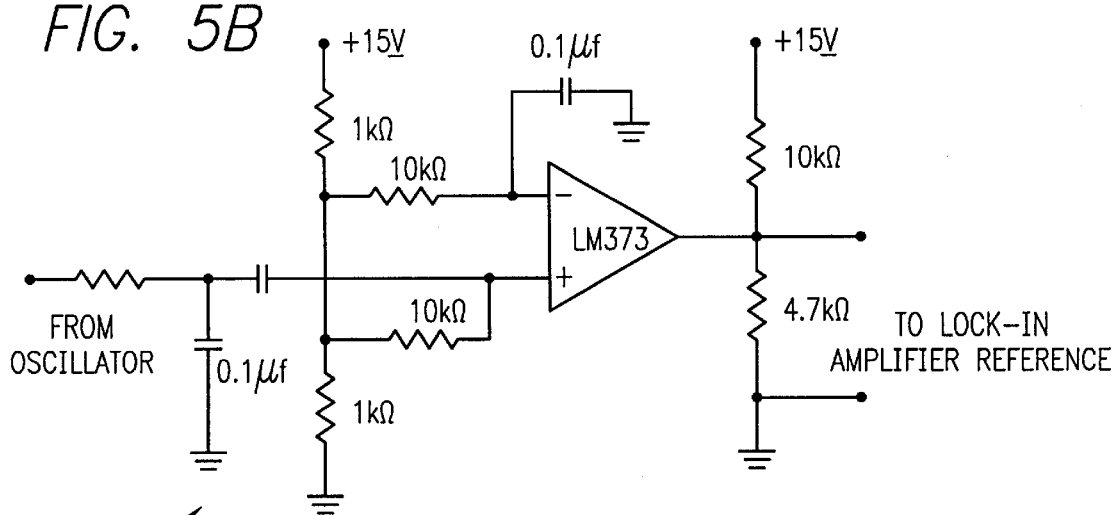
FIG. 5B is a circuit schematic drawing of the signal conditioning in circuit 38 of FIG. 5.
Figure 5C:
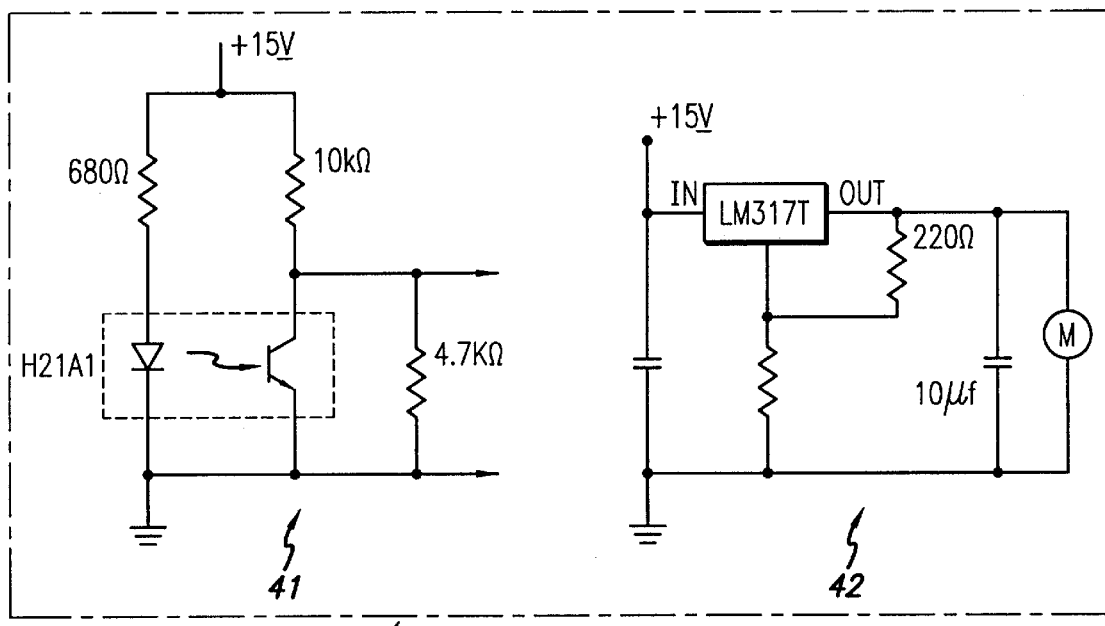
FIG. 5C is a circuit schematic drawing of the chopper circuitry 42 of FIG. 5.
Figure 5D:
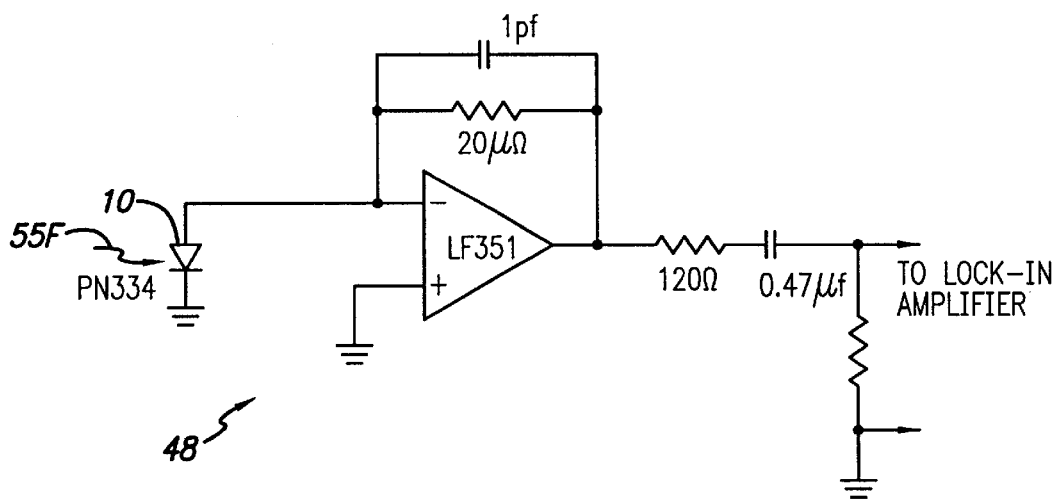
FIG. 5D is a circuit schematic drawing of the photodiode 47 and detector and preamplifier circuitry 48 of FIG. 5.

Light 55F is converted by a photodiode 10 which is sensitive to light having a wavelength from about 400 to 1000 nanometers to a small current. This current is then converted to a voltage using a standard operational amplifier based photodiode preamplifier circuit 48. The output of the photodiode preamplifier 48 is sent to the signal input of a lock-in amplifier 45. The output of oscillator 35 (at about 475 Hz) is "shaped" by the circuit 38 shown in FIG. 5B to provide a clean square wave and is sent to the reference input of the lock-in amplifier 45. A digital meter 46 is used at the lock-in amplifier output to provide a sensitive indication of the null point (zero volts).

The accuracy of this method relies on the capability of determining the applied voltage/current and the precision with which the null reading of the lock-in amplifier 45 can be established. These two readings have been made to a precision that yields the null position to plus or minus 0.0001 degrees, which is clearly satisfactory for the determination of blood glucose levels in the clinically meaningful range.

An alternative method would be to insert two independent modulator/rotators into the optical path, one of them to be excited exclusively by the DC component of activation and the second to be excited solely by the required AC component. This approach could benefit the Faraday rotator methodology in that the AC/DC isolation filters would be replaced by a second coil/rotator element which might be less bulky than the filter components. (The PLZT modulator would not benefit from this implementation. That is, the PLZT device, being voltage driven rather than current driven like the Faraday rotator, would have a much simpler and more compact AC/DC isolation filter and thus would not benefit as much from the modification.)

FIG. 6 shows the precision of measurements of DC current applied to the activation coil of a Faraday rotator as a function of glucose concentration in a 1 centimeter path length cell when the above configuration was employed. The error bars on each data point are 0.002 millivolts and this value is approximately 2 times the line thickness as shown in the graph. Thus both sensitivity and precision are more than adequate for the measurements of sucrose concentrations over the desired range for a 1 centimeter path length.

Usual approaches to non-invasive optical measurements of blood properties, principally oxygen concentrations (oximetry), have concentrated on passing radiation through a finger or on analyzing the reflected radiation. Preliminary analysis shows that the path length through a finger, web of the hand, ear lobe, cheek, tongue, etc. is adequate for the analysis of blood glucose by polarization rotation even though the resultant path length is only a few millimeters.

Such a measurement would be made in the near infrared (NIR) region of the spectrum, which is the region where most organic substances are basically transparent. This region is generally accepted as being between about 700 nanometers and 2000 nanometers.

However, blood, being about 70% water, exhibits strong water absorption characteristics. This absorption begins at a level of about 0.01 $cm^{-1}$ near 730 nanometers and rises to a level of 100 $cm^{-1}$ near 1800 nanometers. Much "structure" in the curve of absorption vs. wavelength exists between 1300 and 1800 nanometers, which will add to the complexity of extracting glucose-related information from absorption measurements. Another complication is the existence of blood-oxygen absorption centered near 680 nanometers and extending to wavelengths of 750 nanometers. Thus the preferred measurement is with wavelengths of about 780 nanometers through 850 nanometers.

The passage of light through tissue is not purely a matter of accounting for optical absorption. Being an inhomogeneous medium, the tissue sample will scatter the radiation as well as absorbing it. This scattering is not quantifiable due to uncertainties in the exact nature of the tissue media.

However, it is known that such scattering will affect the polarization of the transmitted beam. The depolarization of optical beams due to small angle scattering is a well documented phenomenon. The shape of the scattering medium also can have a substantial effect on the depolarization parameters. For example, flat platelets (the shape of red blood cells) have a stronger depolarization effect than round particles. The net effect of such scattering depolarization is to produce a transmitted beam that is not truly linearly polarized, but rather is elliptically polarized. The effect of the elliptical polarization on the measurement in the absence of a quarter wave plate being incorporated into the system is that a true extinction, down to near zero amplitude, is not observed. Rather, as the analyzer is rotated through 180 degrees, one observes a maximum and a non-zero minimum of the detector output signal 11. The magnitude of the minimum of the detector output signal 11 is a measure of the amount of depolarization.

I have made measurements on the transmission through the finger tip including the nail bed, through the finger tip excluding the nail bed, and through the web of the hand between the thumb and the forefinger. Overall measurements at 785 nm indicate transmission levels of $10^{-3}$ to $10^{-4}$ with significant amounts of forward scattering. Utilizing these values together with an extinction ratio of $10^5$ for the polarization spectrometer, it is clear that the true null position will result in a signal level that is well below even the theoretical noise level of room temperature detectors. The transmitted signal levels on the wings of the AC modulated system (refer to FIG. 3 and FIG. 4) are barely above the noise level of the detector system employed here, which is considerably above the theoretical noise level (undoubtedly by a factor of 10 or so). Since a signal to noise ratio of about 1000 is necessary in order to make accurate (5%) measurements in a reasonable time (less than 1 second) it will be necessary to increase the magnitude of the AC modulation drive to the modulator by about a factor of 10. For the case of the Faraday rotator this magnitude of drive current would result in unacceptably large heating of the coil. Thus, the only apparently feasible method of employing a Faraday rotator would be in a "burst" mode in which the coil is activated for a short (0.1 sec) time and then turned off for a longer time period (1 to 5 seconds). Simultaneously, even greater precision requirements are imposed on the stability and precision of the AC modulation voltage amplitude due to the much larger amplitude and its direct effect on the noise level of the DC measurement. A precision of at least one part per million is clearly required.

Thus, the alternative types of modulators (specifically the PLZT-based Kerr cell or the KDP based Pockels cell) are the preferred modulators for this situation since they are a very high impedance load presented to a voltage driver. This results in a very small power dissipation in the polarization modulator. The only remaining problem for these modulators is the stringent precision required of the driving voltage amplitude.

In all considerations it is assumed that careful attention is given to the frequency stability of the AC driving oscillator so that that source of noise is minimized for any case.

This technique of accounting for the scattering depolarization represents a critical component in assuring the successful analysis of blood glucose in vivo through the skin.

Note that the method does not require measurements at two or more wavelengths and thus does not suffer from problems associated with the interference of a varying background level of absorption which has presented such differential absorption approaches with major problems.

The ultimate size of the devices described herein can be quite small. A very small glass rod (2–4 millimeters diameter) can be employed as the active Faraday medium, which would result in a much smaller diameter activation coil. This coil would be wound with smaller diameter wire (#34–#40 gage) and thus could be driven at significantly lower currents. This would result in a very compact device having significantly reduced driving power. Alternatively, a very small Faraday rotator element can be produced by passing the light through an optical fiber which is enclosed by a small toroidal coil. By employing many windings of the fiber inside the toroid, the path length can be greatly increased and thereby compensating for the lower Verdet constant of the fiber's glass. Also a PLZT optical modulator can be made very small. Polarizers and wave plates can be fabricated in very small sizes. Thus, the entire device can be fabricated in a very small package, comparable for example to the size of a small pocket paging device.

By determining the sucrose levels in the aqueous humor, which has been proven to have a good quantifiable relationship to the blood sucrose concentration, it is possible to make the measurement in a simple and direct manner since there would be none of the above mentioned absorption and/or scattering effects which could complicate the measurement.

FIG. 7 shows a cross sectional diagram of the typical human eye 50 together with an indication of one optical path to be utilized for making glucose concentration determinations, as shown in FIG. 1 of the above King et al. article.

In order to cause probing optical radiation 55A to sample the aqueous humor 53 in the anterior chamber of the eye, beam 55A,B,C passes transversely through the anterior chamber in the manner indicated in FIG. 7. Since the cornea/aqueous humor 54 is an optical medium having an index of refraction of about 1.35, the incoming probe beam makes an angle of incidence on the cornea of about 70 degrees, as indicated in the diagram. In this case the parallel probe beam 55B passes through the anterior chamber approximately parallel to the iris, and thus no direct optical radiation is directed into the eye and to the retina. (Any optical radiation which is scattered from optical defects of the cornea and from any floating particulates in the aqueous humor might produce some very small amount of radiation that reaches the retina of the eye through the pupil. This amount of radiation will not be nearly sufficient to cause any retinal damage.)

During experimentation, I determined that there existed an alternate transverse path through the eye's anterior chamber 57. I found that this greatly reduced the experimental complexity of making reliable measurements. This path is illustrated in FIGS. 8A and 8B. In this preferred embodiment, the probing laser radiation 55A enters the anterior chamber 57 in a direction parallel to the eye's iris 56. That is, the probing radiation 55A is approximately parallel to the iris 56. The radiation is refracted toward iris 56, and the optimum sensitivity of measurement is achieved when the laser spot is observed to strike the iris 56 at a point 58 very near the distal point of the iris. A simplistic ray trace of this path reveals that the radiation 55D reflected from point 58 is refracted again by the distal section of the cornea and, due to the symmetry of the cornea 54, it emerges as output beam 55C parallel to the input beam 55A and very nearly collinear with it, within a fraction of a millimeter. This means that the complete optical system can be easily aligned and optimized prior to the start of measurements on the eye.

Since the input beam to the eye and the output beam from the eye are collinear and only displaced from each other by a fraction of a millimeter or less, it is possible to simply align and calibrate the entire optical system without the presence of the eye and/or any other optical structure. This makes the system simple and straightforward to utilize. Note that if the path of FIG. 7 were to be employed, it would be necessary to zero or otherwise initialize the instrument with the eye or some surrogate optical elements in position since the input and output beams are significantly deviated from each other.

I have found that the experimental sensitivity from those subjects tested was nearly the same, within about 5%; this is probably because the human eye does not vary much in size from one individual to another, When the laser beam 55A,B,C,D was transversing the eye's anterior chamber 57, the frontal view of the eye with the visual location of the laser reflection spot 58 on the iris had the distinctive appearance shown in FIG. 8B. With this location of the reflection spot 58, the largest portion of the total path length through the anterior chamber 57 is on the incident, or proximal, side of the point of reflection 58, with only a very small portion 55D occurring following the reflection. This factor is quite important, since the rotational direction of the glucose in the anterior chamber following reflection is opposite to that prior to reflection at point 58. Thus, the portion 55D of the path length following the reflection will "unwind" or cancel the polarization rotation which occurs during portion 55B before reflection. For the above embodiment of the invention, such "unwinding" is negligible. Incidentally, it has been observed experimentally that no radiation is detected optically by individuals in which the blood glucose measurements have been made by this technique.

The spherical shape of the cornea and the location of the iris 56 are such that the output beam 55C and the input beam 55A of FIGS. 8A and 8B are nearly collinear even though the position of the input beam 55A may vary considerably during initial positioning of the modified polarization spectrometer of the present invention. This is apparently because the refracted beam 55B impinges on nearly the same point 58 of iris 56 for such different orientations.

FIG. 8C shows the output signal of detector 10 as the modified polarization spectrometer position is positioned so as to get a detection output signal. Numeral 92 indicates the detector output signal during the initial positioning of the polarization spectrometer, before input beam 55A is properly oriented. The portion of the signal indicated by numeral 92 consists of a several millivolt noise signal on the detection output. Numeral 93 indicates a slightly increased signal on the detection output as the input beam 55A is positioned so that the refracted beam 55B gets closer to a good reflection spot. Numeral 94 indicates a sudden increase in the detector output signal level from roughly zero volts to roughly 25 millivolts when the input beam 55A is positioned so as to produce the path shown in FIG. 8A, with the refracted beam 55B being reflected off of a spot on iris 56, producing the reflected beam 55D in the output beam 55C collinear with the input beam 55A.

I have found that if the subject simply holds still, the signal level indicated by numeral 95 remains steady (with several millivolts of noise superimposed thereon). Typically, 3 to 5 seconds of the signal level 95 is more than adequate for a precise adjustment of the DC balance point current applied to the Faraday rotator as needed to establish a precise value of the polarization rotation due to glucose in the anterior chamber of the eye. Dotted line 96 indicates a return of the detector output signal to essentially zero when the polarization spectrometer device is then moved. It should be noted that the waveform shown in FIG. 8C indicates that there is no problem with ambiguous or "false" output levels that can be mistakenly misinterpreted.

Figure 9A:
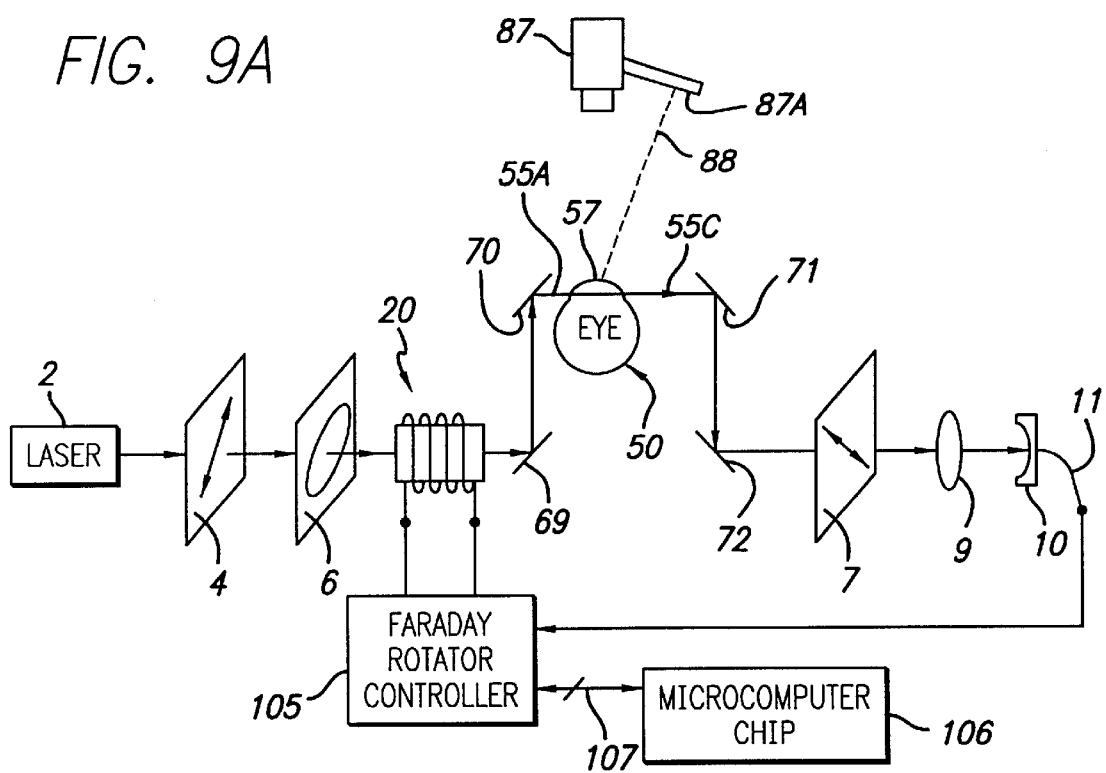
FIG. 9A is a diagram of an apparatus employing turning mirrors to guide a beam to and from the eye as the measurement site.

This situation permitted a unique, simple and very effective feedback method to be employed for assisting the subjects in properly positioning their eyes for high quality measurement, utilizing a branch prototype or model device. The method employed is illustrated by FIG. 9A which provides a description of the apparatus employed in the human experiments. The physical setup includes a first turning mirror 69 which directs the laser beam to a small (5 mm×5 mm) 45 degree turning mirror 70 that directs the beam to the eye's anterior chamber in the transverse manner described above. After transversing the eye's anterior chamber 57, the output beam 55C is intercepted by a second small 45 degree turning mirror 71 which is located on the nasal side of the eye. This mirror redirects the light beam to the final large turning mirror 72 which redirects the output beam 55C to the final analyzer, focusing lens and silicon detector. A camcorder 87 is positioned so that the viewing direction is within about 10 degrees of the normal to the eye and the camera is "zoomed in" so that the subject's eye nearly fills the field of view. The camcorder (Sony Model TRV52 or equivalent) has an associated CCD viewing screen 87A which can be deployed so that the subject can observe what the camera is recording, as indicated by dotted line 88.

During the measurement procedure, the subject focuses on the LCD viewing screen of the camcorder and can clearly observe the position of the laser spot 58 on his own iris. When the above scene diagramed in FIG. 8B is located, the subject then simply "freezes" that sight picture for the duration of the measurement, which is a few seconds. It was also found to be beneficial to the measurement stability if an image of the digital read out of the lock-in amplifier output signal as shown in FIG. 4 was superimposed onto one corner of the LCD viewing screen so that the subject could directly observe the results of the measurement.

Figure 9B:
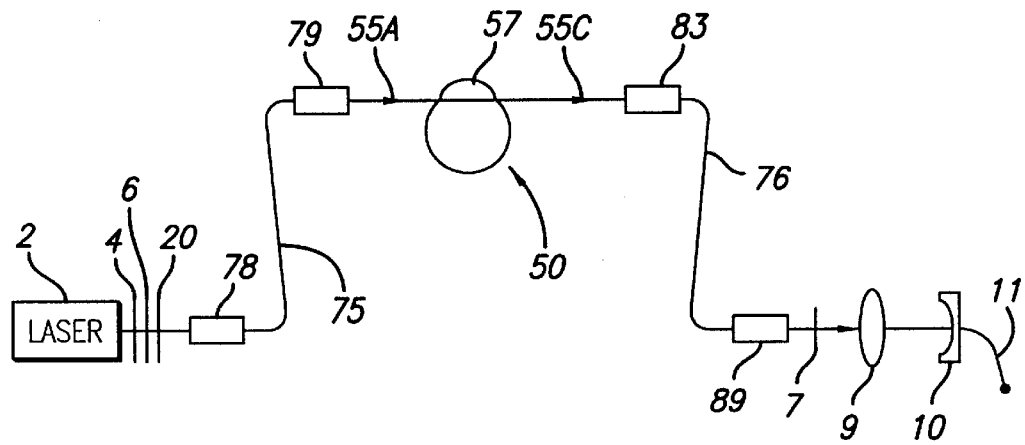
FIG. 9B is a diagram of an apparatus employing a pair of optical fiber collimators to guide the beam to and from the eye as the measurement site.

FIG. 9B illustrates an embodiment of the invention similar to that of FIG. 9A except that fiber optic collimators 78, 79, 83, and 89 are used instead of the various turning mirrors.

Figure 10:
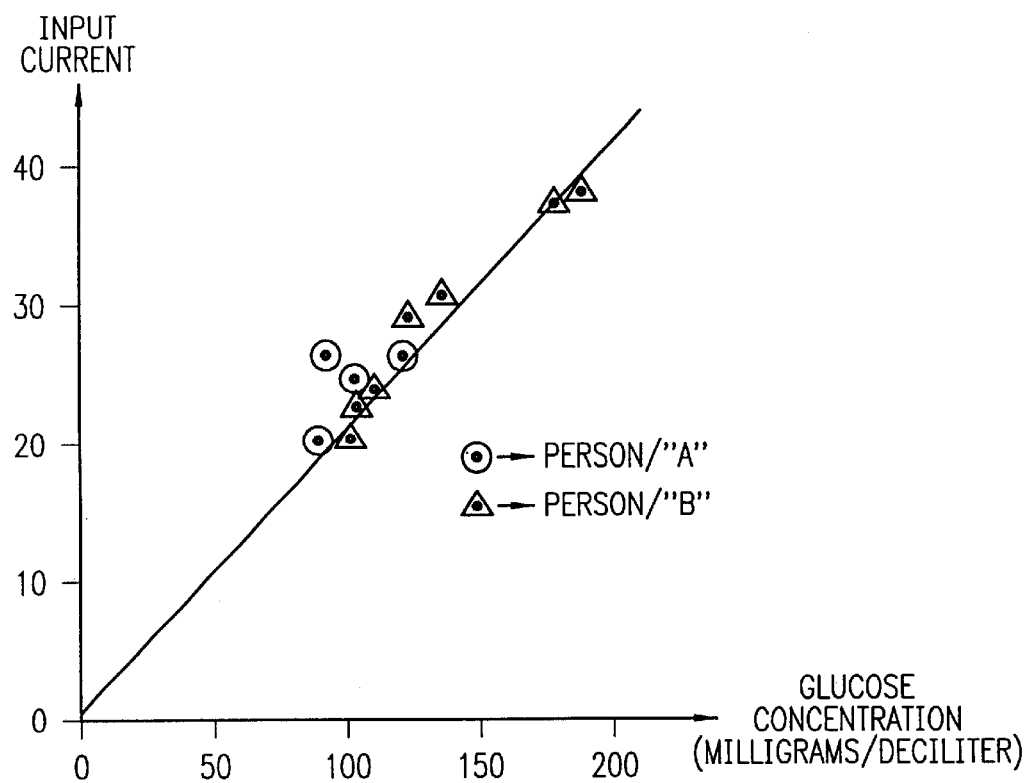
FIG. 10 is a graph indicating in vivo measurements of blood glucose concentrations in several individuals using transmission through the anterior chamber of the eye.

The graph of FIG. 10 shows the experimental measurements of blood glucose concentrations made on two individuals by optical transmission through the anterior chamber of the eye by the method outlined above with reference to FIGS. 8A,B and FIG. 9A. The data are accurate to about 5%.

Figure 11:
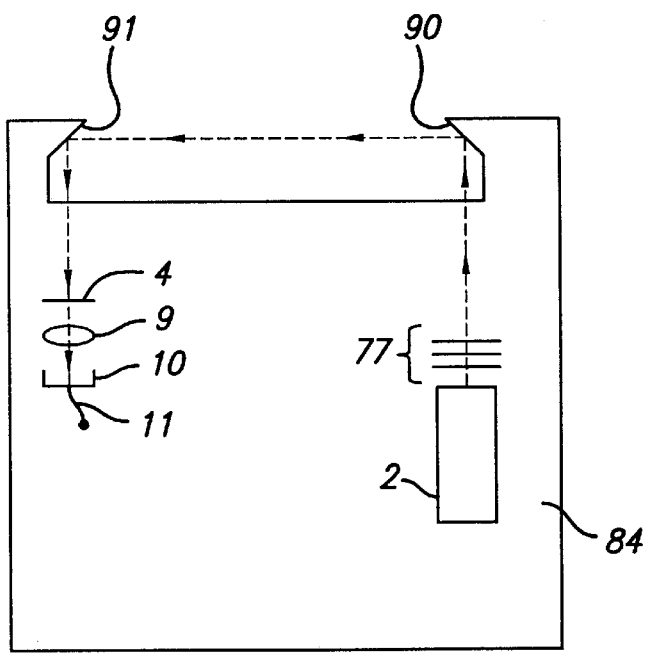
FIG. 11 is a diagram illustrating a hand held embodiment for measurement of glucose concentration in the anterior chamber of the eye.
Figure 12:
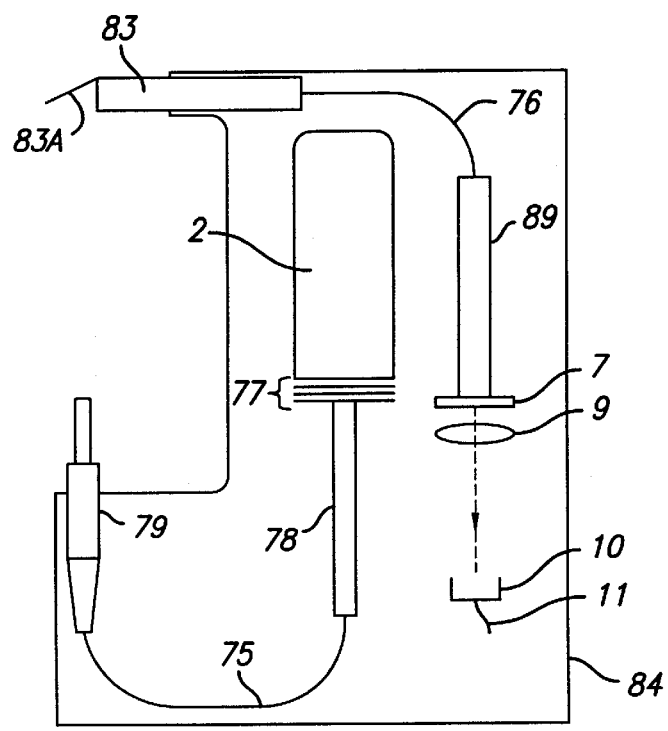
FIG. 12 is a diagram illustrating another hand held embodiment for measurement of glucose concentration in the anterior chamber of the eye.
Figure 13:
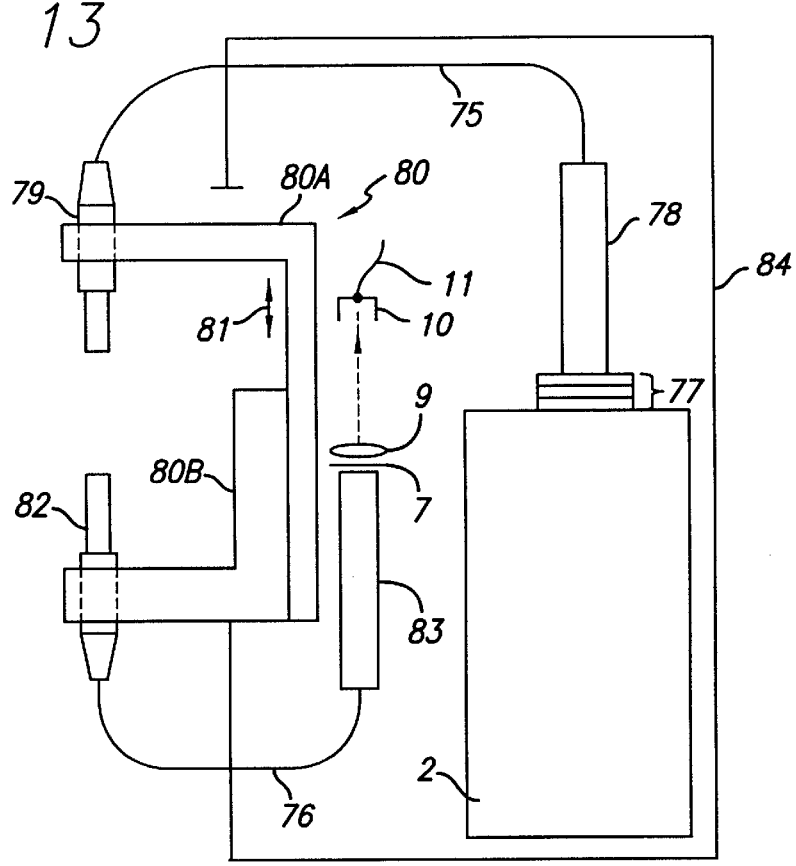
FIG. 13 is a diagram illustrating a hand held embodiment for measurement through the skin of an individual.

FIGS. 11, 12, and 13 show proposed configurations of a miniaturized system based on the designs discussed above.

FIG. 11 shows a design for measurement "through the eye", and employs a miniature laser 2 with an output wavelength of 650 nanometers. Turning mirrors 91 and 92 are employed to route the laser light to and from the eye. The mirror separation is fixed. An electronics package (subsequently described) is configured to fit into available space inside the case. The package dimensions for this design are 3.0 inches wide×3.75 inches long×1.25 inches thick.

FIG. 12 shows a similar, generally equivalent design for measurement "through the eye", and employs a miniature laser 2 with an output wavelength of 650 nanometers. Fiber optic collimators are employed to route the laser light to and from the eye. In this case the probe separation is fixed while the output collimator has a very small 45° turning mirror or prism 83A fastened to the end of a support member near the corner of the eye nearest the nose. The electronics package is configured to fit into available space inside the case, which is about 3.0 inches by 3.75 inches by 1.25 inches.

The polarizers, quarter wave plate, optical modulators, focusing lens, and detector in the embodiment of FIG. 12 can readily be obtained in very small sizes. All detection electronics, including the lock-in amplifier, can be included on one or two integrated circuit chips or in a single ceramic header. The modulator drive system can be fabricated on a small printed circuit board. Small, rechargeable batteries can be used. The overall package design size can be approximately 2.75" inches wide (+1.0 inches for the probe extensions)×4.5 inch high×1.5 inch thick.

FIG. 13 shows the design for a device for measurement "through the skin" and employs a miniature laser 2 with an output wavelength of 820 nanometers. Fiber optic collimators 74, 79, 82 and 83 are employed to route the laser radiation first to the input side of the measurement site and subsequently from the output side of the measurement site to the analyzer 7, focusing lens 9, and detector 10. The input/output (I/O) "probe" separation between fiber optic collimators 79 and 82 is adjustable as indicated by arrows 81 for the individual user by being mounted on a dovetail slide system 80 including stationary member 80B and slide member 80A while at the same time the optical components remain in alignment.

Referring again to FIG. 9A, the DC bias current and AC modulation current are applied to the coil of Faraday rotator 20 by Faraday rotator controller circuit 105, which includes the power supply 30, oscillator 35, current source 31, power amplifier 36, filter circuitry, lock-in amplifier 45, and detector/preamplifier circuit 48 of FIG. 5. Faraday rotator controller circuit 105 is controlled via a bus 107 by a microcomputer chip 106 which operates to automatically perform the initial calibration of the device as shown in FIGS. 11, 12, and 13 by measuring a null in the detector output.

Microcomputer chip 106 also controls the previously described nulling process during the portion 95 of the curve shown in FIG. 8C, and also performs suitable averaging operations to determine an accurate value of the DC shift in the current applied to the coil of Faraday rotator 20 to establish a precise DC null thereof after the anterior chamber of the eye or a suitable tissue sample has been placed in the path of the beam.

Microcomputer chip 106 includes a clock and memory which logs the time, date, and value of each successful glucose concentration measurement by the patient, and effectuate downloading of this information to another computer. Microprocessor chip 106 also assists the patient in initially aligning the hand-held device of FIGS. 11 or 12 up to his or her eye, align a red LED indicator reflected from the eye with a suitable crosshair, indicates when low detection output signal levels as indicated by numerals 92 or 93 in FIG. 8C have been detected, illuminates a yellow LED when the signal level indicated by numeral 95 has been detected to prompt the patient to hold that position, and finally illuminates a green LED when the detector output signal level 95 has been maintained for the time period needed to accomplish the glucose concentration measurement.

The sensitivity of the above embodiments of the invention is demonstrably higher than that reported by Cote et al. in that I have successfully measured glucose levels in the eye's anterior chamber with a single pass rather than resorting to the multiple pass system described in their patent. Also, my approach depends on only a single detector/amplifier system, which is both simpler and lower in noise problems. In contrast to the above mentioned King et al. system, the AC and DC components of polarization rotation are carefully separated and can be treated as independent variables, which considerably reduces the instrumentational complexities and results in a greatly reduced noise level for the entire system. Since the variation of signal intensity near the null position varies as $\sin^2\Delta\theta$ of the offset angle, any noise present in the AC modulation signal from the Pockels cell will show up in the null measurement sensitivity. The AC modulation to achieve nearly 9 degrees of polarization rotation must be compared to the measurement precision requirement of 0.0003 degrees. Thus a stability and noise filtering of the AC drive voltage of about 1 part in 100,000 must be addressed so that it does not constitute a serious noise problem. In the present invention the isolation of AC and DC components of modulator driving systems and attention to noise minimization in both the AC and DC components provides a relatively noise free device and permits a measurement of DC offset voltage to 1 part in 1,000,000 of the AC drive amplitude, in contrast to the prior art.

Unlike the system described in the above mentioned Cote et al. patent, my proposed device has no moving parts and thus is free of any mechanically produced noise problems. My method of employing a high quality quarter wave plate effectively results in a significantly lowered noise level in that the null extinction is of higher quality than that obtainable with the instrumentation described in the above mentioned article by King et al.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention. For example, it is possible that a film covering the cornea, or the cornea itself, may include concentrations of glucose which could be measured by ellipsometric techniques applying the principles of the invention. Furthermore, optically active ingredients other than glucose which effect polarization rotation of a beam in a sample may be measured using the basic techniques of the present invention. The sample may be other than a biological sample. The relative positions of quarter wave plate and the analyzer and the sample can be different than in the described embodiments. The light does not have to be perfectly monochromatic. Theoretically, the initial measurement could be made with the sample in the light path, with the analyzer rotated relative to the polarizer to extinguish the beam reaching the detector, the sample removed, and the DC signal shift needed to again extinguish the beam reaching the detector would represent the glucose concentration in the sample.

What is claimed is:

1. A method of measuring concentration of an optically active substance in the anterior chamber of an eye, comprising the steps of:
    (a) guiding a polarized beam so it is generally parallel to an iris of the eye;
    (b) introducing the beam into the anterior chamber such that it is refracted within the anterior chamber, impinges on the iris, is reflected therefrom, and then exits the anterior chamber approximately collinear with the beam immediately before the point at which it is introduced into the anterior chamber;
    (c) guiding the beam exiting from the anterior chamber through an analyzer and onto a detector; and
    (d) applying a signal to a polarization modulator to extinguish light passing from the analyzer to the detector, the signal representing the concentration of the optically active ingredient in the anterior chamber.

2. The method of claim 1 including the step of adjusting the orientation of a portion of the beam incident on a cornea of the eye until a stable, substantially increased output signal level is produced by the detector.

3. The method of claim 1 wherein the optically active substance includes glucose.

4. The method of claim 1 including calibrating the analyzer to extinguish light passing from the analyzer to the detector before performing step (a).

5. The method of claim 4 wherein step (d) includes simultaneously applying a DC signal and an AC signal to the polarization modulator to extinguish light of the beam to prevent it from passing from the analyzer to the detector by shifting the DC signal to a value that produces a null in the AC component of a corresponding output signal produced by the detector, the value of the shifted DC signal then representing the glucose concentration in the anterior chamber.

6. A method of measuring concentration of an optically active substance in the anterior chamber of an eye, comprising the steps of:
    (a) guiding a beam through a polarizer oriented in a first direction to polarize the light in a first direction, and then through a polarization modulator and an analyzer oriented in the second direction to polarize the light in a second direction, and then guiding the beam from the analyzer to a detector;
    (b) adjusting at least one of the polarizer and the analyzer to extinguish light of the beam to prevent it from passing from the analyzer to the detector;
    (c) guiding the beam, after it passes through the polarizer, so it is generally parallel to an iris of the eye and then introducing the beam into the anterior chamber such that it is refracted within the anterior chamber and impinges on the iris, is reflected therefrom, and then exits the anterior chamber approximately collinear with the beam immediately before the point at which it is introduced into the anterior chamber;
    (d) guiding the beam exiting from the anterior chamber onto the detector; and
    (e) modifying a signal applied to the polarization modulator to extinguish light passing from the analyzer to the detector, the amount of modification of the signal representing the concentration of the optically active ingredient in the anterior chamber.

7. The method of claim 6 including the step of adjusting the orientation of a portion of the beam incident on a cornea of the eye until a stable, substantially increased output signal level is produced by the detector.

8. The method of claim 6 wherein the optically active substance includes glucose.

9. The method of claim 6 wherein step (e) includes simultaneously applying a DC signal and an AC signal to the polarization modulator to extinguish light of the beam to prevent it from passing from the analyzer to the detector by shifting the DC signal to a value that produces a null in the AC component of a corresponding output signal produced by the detector, the value of the shifted DC signal then representing the glucose concentration in the anterior chamber.

10. The method of claim 9 including applying the output signal to an input of a lock-in amplifier and determining that the null has been produced when a DC output of the lock-in amplifier is zero.

11. The method of claim 6 wherein step (a) includes passing the beam through a quarter wave plate after it exits from the polarizer.

12. The method of claim 6 including, before step (a), collimating light from a source to produce the beam.

13. The method of claim 6 wherein the beam is monochromatic.

14. The method of claim 6 wherein step (b) is performed before step (e).

15. The method of claim 9 wherein the polarization modulator includes a Faraday rotator and wherein step (e) includes applying the DC signal with the AC signal superimposed thereon to a coil of the Faraday rotator.

16. The method of claim 15 wherein the DC signal is a DC current having a value in the range of about 0.01 to 100 milliamperes.

17. The method of claim 16 wherein the AC signal is an AC current having a range in the value of about 0.01 to 10 amperes, to thereby reduce noise to the range of a few millivolts or less.

18. A system for measuring concentration of an optically active substance in an anterior chamber of the eye, comprising in combination:
    (a) a light source producing a beam;
    (b) a polarizer oriented in a first direction to polarize light of the beam in a first direction;
    (c) a polarization modulator transmitting the beam after is has passed through the polarizer;
    (d) an analyzer polarizing light from the polarization modulator in a second direction;
    (e) a detector receiving light from the analyzer;
    (f) a first optical structure introducing the beam, after it passes through the polarizer, into the anterior chamber generally parallel to an iris of the eye so that the beam is refracted within the anterior chamber and impinges onto the iris, is reflected from the iris, and then exits the anterior chamber approximately collinear with the introduced beam;

(g) a second optical structure receiving the beam after it exits the anterior chamber and guiding it to the detector; and (h) a polarization modulator control device coupled to a control terminal of the polarization modulator and operative to shift a DC bias signal applied to the polarization modulator to extinguish light of the beam to prevent it from passing from the analyzer to the detector.

19. The system of claim 18 wherein the polarization modulator control device is operative to simultaneously apply a DC signal and an AC signal to the polarization modulator to extinguish any light passing through the analyzer to the detector by shifting the DC signal to a value that extinguishes any AC component of an output signal produced by the detector, the value of the shifted DC signal then representing the concentration of the optically active ingredient in the anterior chamber.

20. The system of claim 18 wherein the optically active substance includes glucose.

21. The system of claim 19 wherein the polarization modulator includes a Faraday rotator and the DC signal with the AC signal superimposed thereon is applied to a coil of the Faraday rotator.

22. The system of claim 21 wherein the DC signal is a DC current having a value in the range of about 0.01 to 100 milliamperes.

23. The system of claim 22 wherein the AC signal is an AC current having a value in the range of about 0.01 to 10 amperes.

24. The system of claim 18 wherein the light source in monochromatic, and further including a collimating lens collimating the beam.

25. The system of claim 19 wherein the polarization modulator includes a Kerr cell.

26. The system of claim 19 wherein the polarization modulator includes a Pockels cell.

27. A method of measuring glucose concentration in a sample, comprising the steps of:

(a) passing a beam of collimated light through a polarizer oriented in a first direction to polarize the light in the first direction, a polarization modulator, an analyzer oriented in a second direction to polarize the light in a second direction, and a focusing lens, and then to a detector;

(b) adjusting at least one of the polarizer and the analyzer to extinguish any light passing from the analyzer to the detector;

(c) locating the sample between the polarizer and the analyzer; and (d) simultaneously applying a DC signal and an AC signal to the polarization modulator to extinguish any light passing from the analyzer to the detector, by shifting the DC signal to a value that produces a null in the AC component of an output signal produced by the detector, the value of the shifted DC signal then representing the glucose concentration in the sample.

28. The method of claim 27 wherein step (a) also includes passing the beam through a quarter wave plate after the polarizer.

29. The method of claim 28 wherein step (d) includes applying the DC signal with the AC signal superimposed thereon to a coil of a Faraday rotator.

30. The method of claim 29 wherein the DC signal is a DC current having a value in the range of about 0.01 to 200 milliamperes.

31. The method of claim 30 wherein the AC signal is an AC current having a value in the range of about 0.01 to 10 amperes, to thereby reduce noise to the range of a few millivolts or less.

32. The method of claim 31 including applying the output signal produced by the detector to an input of a lock-in amplifier, and shifting the DC signal to a value that causes an output of the lock-in amplifier to have no DC component.

33. The method of claim 28 including passing the beam through the aqueous humor of a human eye so that a portion of the beam passing through the aqueous humor is approximately parallel to an iris of the eye.

34. The method of claim 28 including passing the beam through the aqueous humor of a human eye, by providing an input portion of the beam parallel to a tangent to the center of the cornea of the eye, causing the portion of the beam passing through the aqueous humor to be reflected from a point of the iris of the eye, the reflected portion of the beam emerging from the aqueous humor as an output beam which is substantially parallel to the input portion of the beam.

35. The method of claim 34 wherein the output beam is substantially co-linear with the input portion of the beam.

36. A system for measuring glucose concentration in blood in a sample, comprising in combination:

(a) a collimated light source producing a beam;

(b) a polarizer oriented in a first direction to polarize light of the beam in the first direction;

(c) a polarization modulator transmitting light from a quarter wave plate;

(d) an analyzer polarizing light from the polarization modulator in a second direction;

(e) a detector receiving light from the analyzer;

(f) the sample being located between the polarization modulator and the analyzer; and (g) modulator control circuitry coupled to at least one control terminal of the polarization modulator and operative to simultaneously apply a DC signal and an AC signal to the polarization modulator to extinguish any light passing through the analyzer to the detector by shifting the DC signal to a value that extinguishes any AC component of an output signal produced by the detector, the value of the shifted DC signal then representing the glucose concentration in the blood of the sample.

37. The system of claim 36 including a quarter wave plate oriented in the first direction and transmitting the light polarized by the polarizer.

38. The system of claim 37 wherein the modulator includes a Faraday rotator and the DC signal with an AC signal superimposed thereon is applied between the terminals of a coil of the Faraday rotator.

39. The system of claim 38 wherein the DC signal is a DC current having a value in the range of about 0.01 to 100 milliamperes.

40. The system of claim 39 wherein the AC signal is an AC current having a value in the range of about 0.01 to 10 amperes.

41. The system of claim 40 including a lock-in amplifier receiving a reference voltage and the output signal produced by the detector and operative to invert components of that signal lower than the reference voltage, filter a resulting signal including the non-inverted and inverted components of the output signal produced by the detector and filtering that signal.

* * * * *